US00PP26762P2

(12) United States Plant Patent
Dummen

(10) Patent No.: US PP26,762 P2
(45) Date of Patent: May 24, 2016

(54) ***BACOPA* PLANT NAMED 'DUEBAHBUSA'**

(50) Latin Name: *Bacopa hybrida*
Varietal Denomination: Duebahbusa

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 97 days.

(21) Appl. No.: 14/120,885

(22) Filed: Jul. 7, 2014

(51) Int. Cl.
*A01H 5/02* (2006.01)

(52) U.S. Cl.
USPC ..... Plt./485

(58) Field of Classification Search
USPC ..... Plt./485
See application file for complete search history.

*Primary Examiner* — Susan McCormick Ewoldt
(74) *Attorney, Agent, or Firm* — C. A. Whealy

(57) ABSTRACT

A new and distinct cultivar of *Bacopa* plant named 'Duebahbusa', characterized by its compact, mounding and trailing growth habit; vigorous growth habit; freely branching habit; freely flowering habit; and purple violet-colored flowers.

1 Drawing Sheet

Botanical designation: *Bacopa hybrida.*
Cultivar denomination: 'DUEBAHBUSA'.

BACKGROUND OF THE INVENTION

The present invention relates to a new and distinct cultivar of *Bacopa* plant, botanically known as *Bacopa hybrida* and hereinafter referred to by the name 'Duebahbusa'.

The new *Bacopa* plant is a product of a planned breeding program conducted by the Inventor in Rheinberg, Germany. The objective of the breeding program is to create new compact and freely branching *Bacopa* plants with numerous attractive flowers.

The new *Bacopa* plant originated from a cross-pollination made by the Inventor in Rheinberg, Germany in July, 2011 of a proprietary selection of *Bacopa hybrida* identified as code number F-019-0702, not patented, as the female, or seed, parent with a proprietary selection of *Bacopa hybrida* identified as code number S10-1118-002, not patented, as the male, or pollen, parent. The new *Bacopa* plant was discovered and selected by the Inventor as a flowering plant from within the progeny of the stated cross-pollination in a controlled greenhouse environment in Rheinberg, Germany in May, 2013.

Asexual reproduction of the new *Bacopa* plant cuttings in a controlled greenhouse environment in Rheinberg, Germany since June, 2013, has shown that the unique features of this new *Bacopa* plant are stable and reproduced true to type in successive generations.

SUMMARY OF THE INVENTION

Plants of the new *Bacopa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duebahbusa'.

These characteristics in combination distinguish 'Duebahbusa' as a new and distinct *Bacopa* plant:

1. Compact, mounding and trailing growth habit.
2. Vigorous growth habit.
3. Freely branching habit.
4. Freely flowering habit.
5. Purple violet-colored flowers.

Plants of the new *Bacopa* can be compared to plants of the female parent selection. Plants of the new *Bacopa* differ primarily from plants of the female parent selection in plant habit as plants of the new *Bacopa* are more compact than plants of the female parent selection. In addition, plants of the new *Bacopa* have lighter-colored flowers.

Plants of the new *Bacopa* can be compared to plants of the male parent selection. Plants of the new *Bacopa* differ primarily from plants of the male parent selection in plant habit as plants of the new *Bacopa* are more compact than plants of the male parent selection. In addition, plants of the new *Bacopa* and the male parent selection differ in flower color as plants of the male parent selection have white-colored flowers.

Plants of the new *Bacopa* also can be compared to plants of the *Bacopa* 'Scopia Gulliver Blue', not patented. In side-by-side comparisons conducted in Rheinberg, Germany, plants of the new *Bacopa* differed primarily from plants of 'Scopia Gulliver Blue' in the following characteristics:

1. Plants of the new *Bacopa* were more compact than plants of 'Scopia Gulliver Blue'.
2. Plants of the new *Bacopa* had smaller leaves than plants of 'Scopia Gulliver Blue'.
3. Plants of the new *Bacopa* and 'Scopia Gulliver Blue' differed slightly in flower color.
4. Plants of the new *Bacopa* had shorter peduncles than plants of 'Scopia Gulliver Blue'.

BRIEF DESCRIPTION OF THE PHOTOGRAPH

The accompanying colored photograph illustrates the overall appearance of the new *Bacopa* plant showing the colors as true as it is reasonably possible to obtain in colored reproductions of this type. Colors in the photograph may differ slightly from the color values cited in the detailed botanical description which accurately describe the colors of the new *Bacopa* plant.

The photograph comprises a side perspective view of a typical flowering plant of 'Duebahbusa' grown in a container.

DETAILED BOTANICAL DESCRIPTION

The aforementioned photograph and following observations, measurements and values describe plants grown during the summer in 10.5-cm containers in a glass-covered greenhouse in Rheinberg, Germany and under cultural practices typical of commercial *Bacopa* production. During the production of the plants, day and night temperatures averaged 18° C. and light levels averaged 4,500 lux. Plants were pinched one time three weeks after planting and were 13 weeks old when the photograph and the description were taken. In the description, color references are made to The Royal Horticultural Society Colour Chart, 2007 Edition, except where general terms of ordinary dictionary significance are used.

Botanical classification: *Bacopa hybrida* 'Duebahbusa'.

Parentage:

*Female, or seed, parent.*—Proprietary selection of *Bacopa hybrida* identified as code number F-019-0702, not patented.

*Male or pollen parent.*—Proprietary selection of *Bacopa hybrida* identified as code number S10-1118-002, not patented.

Propagation:

*Type.*—By cuttings.

*Time to initiate roots, summer.*—About five days at temperatures about 20° C.

*Time to initiate roots, winter.*—About seven days at temperatures about 20° C.

*Time to produce a rooted young plant, summer.*—About three weeks at temperatures about 20° C.

*Time to produce a rooted young plant, winter.*—About four weeks at temperatures about 20° C.

*Root description.*—Fine, fibrous; white in color.

*Rooting habit.*—Freely branching; dense.

Plant description:

*Plant and growth habit.*—Compact, mounded and trailing plant habit; vigorous growth habit.

*Branching habit.*—Freely branching habit about seven lateral branches developing per plant; pinching enhances branching potential.

*Plant height.*—About 11.5 cm.

*Plant diameter (area of spread).*—About 66 cm.

Lateral branch description:

*Length.*—About 46.5 cm.

*Diameter.*—About 2 mm.

*Internode length.*—About 2.1 cm.

*Strength.*—Strong.

*Texture.*—Pubescent.

*Color.*—Close to 144B.

Leaf description:

*Arrangement.*—Opposite, simple.

*Length.*—About 1.6 cm.

*Width.*—About 2 cm.

*Shape.*—Ovate.

*Apex.*—Acuminate.

*Base.*—Obtuse.

*Margin.*—Crenulate.

*Texture, upper and lower surfaces.*—Sparsely pubescent.

*Venation pattern.*—Pinnate.

*Color.*—Developing leaves, upper surface: Close to 143A. Developing leaves, lower surface: Close to 143C. Fully expanded leaves, upper surface: Close to 137A; venation, close to 143B. Fully expanded leaves, lower surface: Close to 138A; venation, close to 143C.

*Petioles.*—Length: About 5.9 mm. Diameter: About 2 mm. Texture, upper and lower surfaces: Pubescent. Color, upper and lower surfaces: Close to 144B.

Flower description:

*Flower arrangement.*—Single rotate flowers; freely flowering habit with potentially about 70 to 80 flowers developing per plant; flowers face mostly upright.

*Fragrance.*—None detected.

*Natural flowering season.*—Plants begin flowering about six weeks after planting and flower continuously year-round in moderate climates.

*Flower longevity.*—Flowers last about one week on the plant; flowers not persistent.

*Flower diameter.*—About 2.3 cm.

*Flower length (height).*—About 1.2 cm.

*Throat diameter.*—About 5 mm.

*Tube length.*—About 1.1 cm.

*Flower buds.*—Length: About 5.6 mm. Diameter: About 3.8 mm. Shape: Spatulate. Color: Close to 142C.

*Petals.*—Quantity per flower: Corolla consists of five petals fused at the base. Lobe length: About 9 mm. Lobe width: About 9 mm. Lobe shape: Obovate. Lobe apex: Obtuse, rounded. Lobe margin: Entire. Texture: Petal lobes, upper and lower surfaces: Smooth, glabrous. Throat: Smooth, glabrous. Tube: Smooth, glabrous. Color: Petal lobes, when opening, upper surface: Close to 90C. Petal lobes, when opening, lower surface: Close to 91C. Petal lobes, fully opened, upper surface: Close to N82A; color becoming closer to 89B with development. Petal lobes, fully opened, lower surface: Close to 84A and 84D; color becoming closer to 88B with development. Throat: Close to 23A. Tube: Close to 15A and 142D.

*Sepals.*—Appearance: Five sepals fused into a tubular calyx. Length: About 6.4 mm. Width: About 1 mm. Shape: Lanceolate. Apex: Acute. Margin: Entire. Texture, upper and lower surfaces: Smooth, glabrous. Color, upper and lower surfaces: Close to 143B.

*Peduncles.*—Length: About 7.4 mm. Diameter: About 1 mm. Angle: Mostly upright. Strength: Strong. Texture: Smooth, glabrous. Color: Close to 143C.

*Reproductive organs.*—Androecium: Stamen number: About four. Filament length: About 9.2 mm. Filament color: Close to 149D. Anther shape: Cylindrical. Anther length: About 1 mm. Anther color: Close to 2D. Amount of pollen: Abundant. Pollen color: Close to 12A. Gynoecium: Pistil length: About 1.2 cm. Style length: About 1 mm. Style color: Close to 144D. Stigma color: Close to 150B. Ovary color: Close to 144B.

*Seeds & fruits.*—Seed and fruit production have not been observed on plants of the new *Bacopa*.

Temperature tolerance: Plants of the new *Bacopa* have been observed to tolerate temperatures from about 5° C. to about 40° C.

Pathogen & pest resistance: Plants of the new *Bacopa* have not been shown to be resistant to pathogens and pests common to *Bacopa* plants.

It is claimed:

1. A new and distinct *Bacopa* plant named 'Duebahbusa' as illustrated and described.

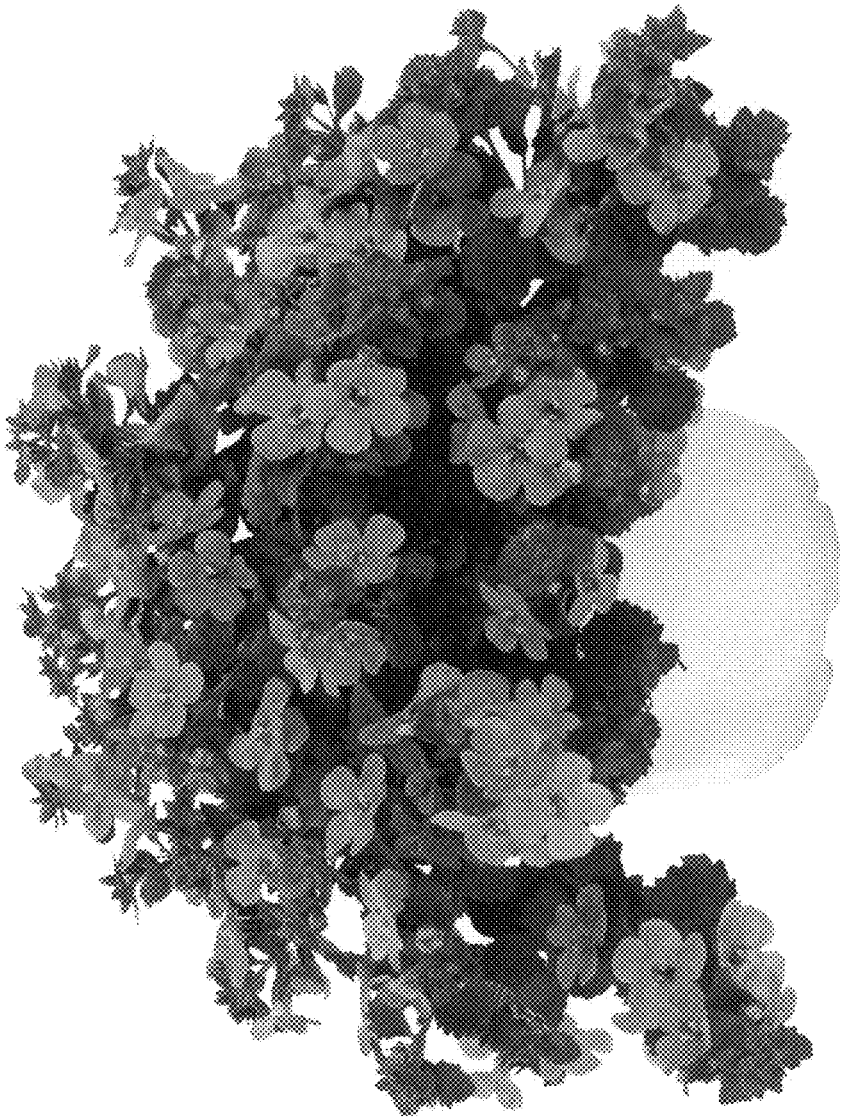

* * * * *